United States Patent [19]

Myers

[11] 4,355,041
[45] Oct. 19, 1982

[54] 4,5-BIS-(4-FLUOROPHENYL)-1-(4-NITROBENZYL)-2-[((1,1,2,2-TETRAFLUOROETHYL)SULFONYL]-1H-IMIDAZOLE, COMPOSITION AND USE

[75] Inventor: Melvyn J. Myers, Wilmington, Del.

[73] Assignee: E. I. Du Pont de Nemours and Company, Wilmington, Del.

[21] Appl. No.: 336,764

[22] Filed: Jan. 4, 1982

[51] Int. Cl.³ ............... A61K 31/415; C07D 233/84
[52] U.S. Cl. ............................ 424/273 R; 548/337
[58] Field of Search ....................................... 548/337

[56] References Cited

U.S. PATENT DOCUMENTS 3,651,080  3/1972  Doebel et al. ............... 260/309
4,182,769  1/1980  Cherkofsky et al. ......... 424/273
4,190,666  3/1980  Cherkofsky et al. ......... 424/274

Primary Examiner—Robert W. Ramsuer

[57] ABSTRACT

This invention relates to a Tetrafluoroethyl Imidazole compound which shows potent antiinflammatory activity.

3 Claims, No Drawings

4,5-BIS-(4-FLUOROPHENYL)-1-(4-NITROBEN-ZYL)-2-[((1,1,2,2-TETRAFLUOROETHYL)SUL-FONYL]-1H-IMIDAZOLE, COMPOSITION AND USE

BACKGROUND OF THE INVENTION

This invention relates to an antiinflammatory imidazole.

There is a continuing need for safe and effective antiinflammatory agents. Inflammation is a disease process characterized by redness, fever, swelling, and pain. Arthritis, in its various forms, is the most prevalent, chronic, and severe of the inflammatory diseases. Traumatic injury and infection also involve inflammation, and antiinflammatory drugs are often used in their treatment.

U.S. Pat. No. 3,651,080 describes 4-alkyl-2-alkylthio-5-aryl-1-substituted-imidazoles as antiinflammatory agents.

U.S. Pat. No. 4,182,769 describes antiinflammatory 4,5-diaryl-2-haloalkylsulfonyl-1-substituted-imidazoles.

Cherkofsky et al., U.S. Pat. No. 4,190,666 discloses antiinflammatory 4,5-diaryl-substituted imidazoles of the formula:

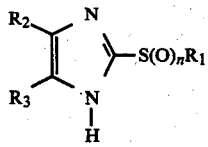

where $R_1$, $R_2$ and $R_3$ represent various defined groups; and n is an integer of 0–2.

The usefulness of most commercial antiinflammatories is limited because of toxicity and adverse side-effects. Many produce gastric irritation and other effects, such as changes in blood cells and central nervous system. Adreno-cortical steroids produce gastric irritation and suppression of normal adrenal function.

The present invention results from efforts to develop new antiarthritic compounds with good antiinflammatory activity and minimal side effects that could be more effective in treating arthritis than are presently available drugs.

SUMMARY OF THE INVENTION

This invention relates to a compound as shown in Formula I, pharmaceutical compositions containing it, and methods of use of this compound to treat inflammation.

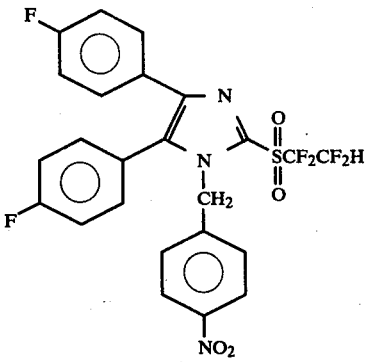

The compound exhibits potent antiarthritic activity.

Synthesis

The following illustrates the synthesis of 4,5-bis-(4-fluorophenyl)-1-(4-nitrobenzyl)-2-[(1,1,2,2-tetrafluoroethyl)sulfonyl]-1H-imidazole:

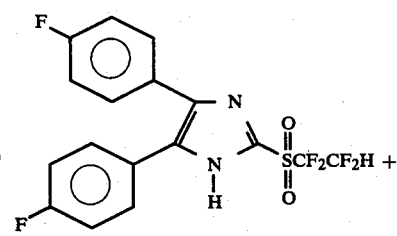

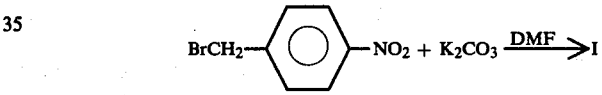

The starting material, 4,5-bis-(4-fluorophenyl)-2-[(1,1,2,2-tetrafluoroethyl)sulfonyl]-1H-imidazole is prepared according to the method described in U.S. Pat. No. 4,190,666. This material is then reacted with a 4-nitrobenzylhalide (chloride or bromide) in the presence of an inorganic base, such as potassium carbonate or sodium carbonate, or an organic base, such as triethylamine. A small amount of an inorganic iodide, such as sodium iodide or potassium iodide, can be added to catalyze the reaction. The reaction is run in a polar aprotic solvent, such as dimethylformamide, dimethylsulfoxide, or N-methylpyrrolidinone at a temperature of from 50° C. to 90° C. for about 4–24 hours.

EXAMPLE 1

4,5-Bis-(4-fluorophenyl)-1-(4-nitrobenzyl)-2-[(1,1,2,2-tetrafluoroethyl)sulfonyl]-1H-imidazole 4.20 g (0.01 mole) of 4,5-bis-(4-fluorophenyl)-2-[(1,1,2,2-tetrafluoroethyl)sulfonyl]-1H-imidazole, prepared according to the method described in U.S. Pat. No. 4,190,666, 2.7 g (0.0125 mole) of 4-nitrobenzylbromide, 1.73 g (0.0125 mole) of anhydrous powdered potassium carbonate, and 50 ml of dimethylformamide were combined in a round bottom flask and stirred and heated under nitrogen in an oil bath at 75° C. for 20 hours. The reaction mixture was cooled to room temperature and poured into 500 ml of water. The product was extracted with methylene chloride. The methylene chloride solution was washed several times with water to remove dimethylformamide, dried over sodium sulfate, filtered, and evaporated on a rotary evaporator. The remaining oil was triturated with ether, which caused the product to crystallize. The white solid was filtered, washed with ether, and dried to yield 4.9 g, m.p. 169°–170°. The product was freed from a small amount, usually less than 1% of 4,5-bis-(4-fluorophenyl)-2-[(1,1,2,2-tetrafluoroethyl)sulfonyl]-1H-imidazole by dissolving it in a small amount of methylene chloride and putting the solution through a preparative liquid chromatography apparatus using toluene to elute. After evaporating the toluene from the main fraction on a rotary evaporator, 4.4 g of product, m.p. 176°–177° was obtained. A mass spectrum of the product showed it to have a m/e of 555.4 and also showed it to contain no measurable starting imidazole, m/e 420.3.

Dosage Forms

The antiarthritic agent of this invention can be administered to treat arthritis by any means that produces contact of the active agent with the agent's site of action in the body of a mammal. It can be administered by any conventional means available for use in conjunction with pharmaceuticals; either as an individual therapeutic agent or in combination with other therapeutic agents. It can be administered alone, but is generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.005 to 20 milligrams per kilogram of body weight. Ordinarily 0.05 to 10, and preferably 0.1 to 5 milligrams per kilogram per day given in divided doses 2 to 4 times a day or in sustained release form is effective to obtain desired results.

Dosage forms (compositions) suitable for internal administration contain from about 1.0 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid, either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in *Remington's Pharmaceutical Sciences*, E. W. Martin, a standard reference text in this field.

Useful pharmaceutical dosage forms for administration of the compound of this invention can be illustrated as follows:

Capsules

A large number of unit capsules are prepared by filling standard two-piece hard gelatin capsules, each with 25 milligrams of powdered active ingredient, 200 milligrams of lactose, 24 milligrams of talc, and 6 milligrams magnesium stearate.

A mixture of active ingredient in soybean oil is prepared and injected by means of a positive displacement pump into gelatin to form soft gelatin capsules containing 25 milligrams of the active ingredient. The capsules are washed in petroleum ether and dried.

Tablets

A large number of tablets are prepared by conventional procedures so that the dosage unit is 25 milligrams of active ingredient, 0.2 milligrams of colloidal silicon dioxide, 5 milligrams of magnesium stearate, 275 milligrams of microcrystalline cellulose, 11 milligrams of cornstarch and 123.8 milligrams of lactose. Appropriate coatings may be applied to increase palatability or delay absorption.

Injectable

A parenteral composition suitable for administration by injection is prepared by stirring 1.5% by weight of active ingredient in water with 0.75% sodium carboxymethylcellulose, 0.04% polysorbate 80, 0.9% benzyl alcohol, and 1.8% sodium chloride. The preparation is made sterile by autoclaving or other suitable techniques.

Suspension

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Use

To detect and compare the antiinflammatory activity of the present compound and that of standard drugs, a test was used based on a standard model of arthritis for which there is good correlation with human efficacy. The model is adjuvant-induced arthritis in rats. Federation Proceedings, Vol. 32, No. 2, 1973, "Models Used for the Study and Therapy of Rheumatoid Arthritis"-Symposium of the American Society for Pharmacology and Experimental Therapeutics-states "The rat polyarthritis produced by intradermal injection of a suspension of *Mycobacterium tuberculosis* is mineral oil (adjuvant) has been used extensively for the screening of drugs of potential use in rheumatoid arthritis."

The compound of this invention shows activity in adjuvant-induced arthritis in rats which is widely recognized as a good model of human rheumatoid arthritis.

Methods

Established Adjuvant-Induced Arthritis in Rats

Lewis (Wistar) male rats (Charles River Breeding Laboratories, Wilmington, Mass.) weighing 175–220 grams were injected subcutaneously with 0.1 ml of adjuvant in plantar area of the right hind paw. The adjuvant was prepared by bead-milling, heat-killed, lyophilized *Mycobacterium butyricum* (Difco #0640) in light mineral oil (Fisher Scientific Co. #0-119 Paraffin Oil-Saybolt Viscosity 125/135) 5 mg/ml. Twenty non-arthritic control rats were injected with mineral oil. The animals received water and Wayne Lab-Blox ad libitum*.

*while on a 10-hour light-14 hour-dark cycle

The rats were held for 14 days to allow the development of polyarthritis. The volume of the uninjected, left hind paw of each rat was measured by using a Ugo Basile Volume Differential Meter, Model 7101. Adjuvant injected rats showing no evidence of arthritis were discarded and the arthritic rats were distributed into groups of 10 having equal mean paw volumes with equal standard deviation. Non-arthritic (oil-injected) control rats were distributed into 2 groups of 10. Suspensions of the test compound were prepared for dosing by bead-milling (4 mm glass beads in rubber stoppered serum bottles) for 4–5 hours in aqueous 1% polyvinyl alcohol, 5% gum acacia and 0.5% methyl-paraben.

The test compound was given orally by gavage once daily for 7 days (days 14–20). The 2 groups of oil injected, non-arthritic control rats and the 2 groups of arthritic control rats received vehicle only for 7 days. Paw volumes (uninjected left hind paw) were measured 20 hours after the last dose (on day 21).

Percent decrease from control mean paw volume was calculated with the following formula:

$$\frac{\text{Arthritic Vehicle Control Mean Paw Volume (ml)} - \text{Arthritic Treatment Mean Paw Volume (ml)}}{\text{Arthritic Vehicle Control Mean Paw Volume (ml)} - \text{Non-Arthritic Vehicle Control Mean Paw Volume (ml)}} \times 100 =$$

% Decrease from Control Mean Paw Volume.

Dose-response regression lines of the percent decrease were plotted on semi-log paper and the $ED_{50}$ percent for decrease from control paw volume is estimated by inspection. Data obtained from two separate experiments, as described above, was so plotted. From one experiment, the adjuvant induced arthritis $ED_{50}\%$ for the compound of this invention was estimated to be 0.14. From the second experiment, the adjuvant induced arthritis $ED_{50}\%$ was estimated to be 1.5 mg/kg. The difference between the two results has not been resolved, but polymorphism of the prepared compound samples is thought to be the reason.

What is claimed is:

1. A compound of the formula:

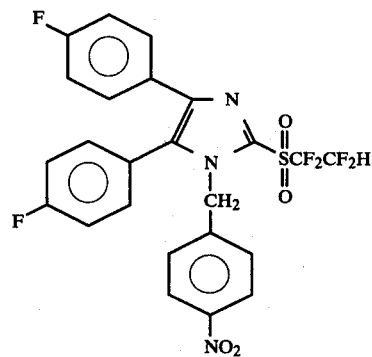

2. A pharmaceutical composition consisting essentially of a suitable pharmaceutical carrier and an effective antiinflammatory amount of the compound of claim 1.

3. A method of treating inflammation in a mammal which comprises administering to the mammal an antiinflammatory amount of the compound of claim 1.

* * * * *